United States Patent [19]

Klemm

[11] Patent Number: Plant 6,447

[45] Date of Patent: Dec. 6, 1988

[54] CARNATION NAMED KLEMAXI

[76] Inventor: Siegfried Klemm, Hanfacker 8, D 7000 Stuttgart 50, Fed. Rep. of Germany

[21] Appl. No.: 939,363

[22] Filed: Dec. 3, 1986

[51] Int. Cl.[4] ..... A01H 5/00
[52] U.S. Cl. ..... Plt./70
[58] Field of Search ..... Plt./70

*Primary Examiner*—Robert E. Bagwill
*Attorney, Agent, or Firm*—Charles W. Rummler

[57] ABSTRACT

A new variety of carnation plant distinguished by its profuse production of bright, vibrant, sulfur yellow flowers which are borne singly on strong, upright pedicels, which are carried on sturdy upright peduncles about 80 cm. long.

1 Drawing Sheet

BACKGROUND OF THE NEW PLANT

This new carnation variety originated at Stuttgart, West Germany, as a sport of an unpatented carnation variety named "Pallas Londorga", being grown in my greenhouses for the production of cut flowers, as well as for propagation and sale of plants to commercial growers for standard carnations. This sport was discovered by me in my greenhouses at Stuttgart in 1980 and was selected for propagation because of its precocity and its vibrant, brilliant sulfur yellow coloration of its flowers. Asexual propagation of this new plant, by means of cuttings, has been carried out at Stuttgart, West Germany and in Italy and in Israel, by me and under my direction through successive generations and the distinctive characteristics of this plant have been found to hold true from generation to generation and appear to be firmly fixed.

DESCRIPTION OF THE DRAWINGS

My new carnation variety is illustrated by the accompanying full color photographic drawing, which shows the inflorescence of a fully open flower, including the view of a bud that is opening.

DESCRIPTION OF THE NEW PLANT

The following is a detailed description of my new carnation cultivar based upon observation of plants growing under conventional greenhouse procedures, the color designation being according to The H.C.C. Colour Chart of Robert F. Wilson issued by the British Colour Council in collaboration with The Royal Horticultural Society of London, England.

THE PLANT

Origin: Sport.
Parentage: The cultivar named "Pallas Londorga".
Classification:
- *Botanic.*—*Dianthus caryophyllus.*
- *Commercial.*—Standard.

Form: Bush.
Height: About 150 cm. to about 170 cm.
Growth: Vigorous and upright with outstanding strength.
Branching: Normal.
Foliage:
- *Quantity.*—Moderate.
- *Leaf size.*—Moderate.

- *Leaf shape.*—Oblong with entire margins.
- *Texture.*—Smooth.
- *Color.*—Upper side — Blue-green. Under side — Blue-green.

THE BUD

Size: Medium, about 20 mm. in diameter and about 40 mm long.
Form: Generally ovoid.
Opening rate: Moderate.
Color:
- *When sepals first divide.*—HCC 1.
- *When petals begin to unfurl.*—HCC 1.

Sepals:
- *Condition.*—Curl back.
- *Number.*—About 5–6.
- *Color.*—Inside — Light-green. Outside — Gray-green.

Calyx:
- *Shape.*—Cylindrical.
- *Size.*—Moderate, about 20 mm. broad and about 25 mm. long.
- *Splitting.*—The calyx does not split.
- *Aspect.*—Smooth.
- *Peduncle.*—Rigid and upright.
- *Length.*—About 80 cm.
- *Color.*—Blue-green.

THE FLOWER

Blooming habit: Continuous and profuse.
Size of bloom: Medium.
- *Diameter.*—About 75 mm. to about 80 mm.
- *Depth.*—About 40 mm. to about 45 mm.

Borne: Singly on strong, upright stems.
Shape: Flat when the bloom opens and high centered when the flower matures.
Petalage:
- *Number of petals.*—About 44 to about 50.
- *Arrangement.*—Generally imbricated.
- *Shape.*—Fan-shaped with toothed margins.
- *Color.*—Both outer and inside petals — HCC 1. In the summer the color may pale.
- *Texture.*—Soft.
- *Appearance.*—Shiny.

Peduncle: Sturdy and upright.
- *Length.*—About 80 cm.
- *Color.*—Blue-green.

Persistence: The flowers hang on and dry and the bloom stays upright.

Disease resistance: Resistance to *Fusarium oxysporum* as observed in the Netherlands, France, Italy and Germany.

Fragrance: None.

Lasting quality:

*On plant.*—About 15 days.

*As a cut flower.*—About 12 days.

REPRODUCTIVE ORGANS

Stamens:

*Number.*—About 12 to about 15.

*Anthers.*—Color — Yellow.

*Filaments.*—About 10 mm. to about 15 mm. Color — Yellow.

*Pollen.*—Color — Yellow.

Pistils: About 3 in number.

*Styles.*—Length — about 20 mm. to about 40 mm. Color — White.

*Stigmas.*— *Color* — *White.*

Fruit: Fertile.

*Shape.*—Ovoid.

*Color.*—Green/Brown at maturity.

This new carnation variety somewhat resembles the variety Pallas londorga. However, it has a different flower color and has no red stripes on the flower.

I claim:

1. A new and distinct carnation cultivar, substantially as herein shown and described, characterized by its high productivity of brilliant sulphur yellow colored flowers, the flowers being borne singly on rigid and erect pedicels carried on sturdy, upright peduncles about 80 cm. long.

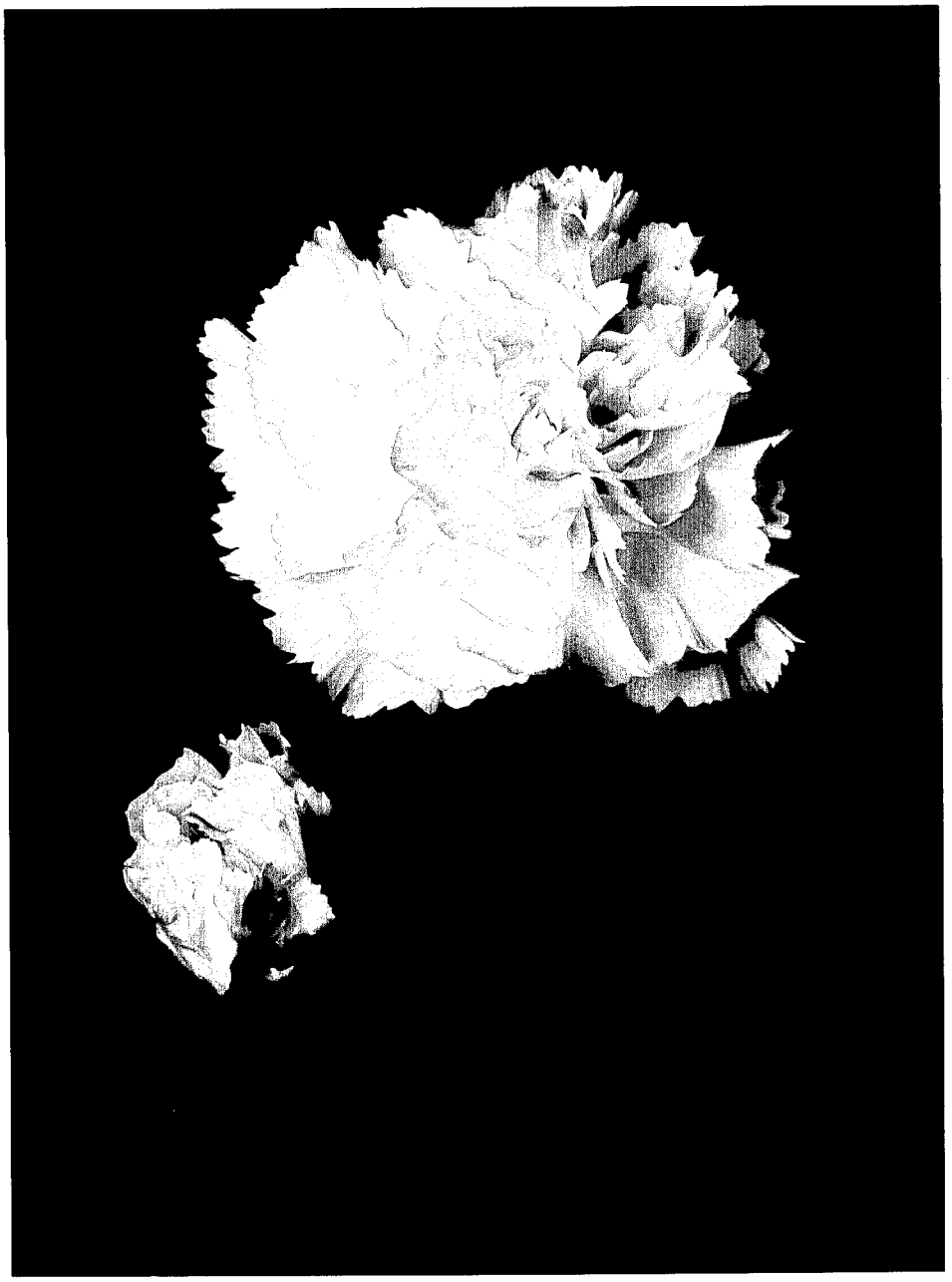

* * * * *